(12) United States Patent
Doke et al.

(10) Patent No.: US 10,632,045 B1
(45) Date of Patent: Apr. 28, 2020

(54) SECURE PORTABLE PILL CANISTER FOR ORDER FULFILLMENT

(71) Applicant: Cornerstone Automation Systems, LLC, Frisco, TX (US)

(72) Inventors: Michael J. Doke, Frisco, TX (US); Don Edward Moonis, Frisco, TX (US); Brandon Lee Roby, Frisco, TX (US)

(73) Assignee: Cornerstone Automation Systems, LLC, Frisco, TX (US)

( * ) Notice: Subject to any disclaimer, the term of this patent is extended or adjusted under 35 U.S.C. 154(b) by 239 days.

(21) Appl. No.: 15/210,292

(22) Filed: Jul. 14, 2016

Related U.S. Application Data

(60) Provisional application No. 62/192,276, filed on Jul. 14, 2015.

(51) Int. Cl.
*A61J 7/00* (2006.01)
*A61J 1/03* (2006.01)
*B65D 83/04* (2006.01)
*B65D 43/02* (2006.01)
*B65D 55/02* (2006.01)
*G06F 19/00* (2018.01)

(52) U.S. Cl.
CPC .............. *A61J 7/0084* (2013.01); *A61J 1/03* (2013.01); *B65D 43/02* (2013.01); *B65D 55/02* (2013.01); *B65D 83/0481* (2013.01); *G06F 19/3462* (2013.01)

(58) Field of Classification Search
CPC ....... A61J 7/0084; A61J 1/03; B65D 83/0481; B65D 43/02; B65D 55/02; G06F 19/3462

USPC ................................... 700/231–244; 221/154
See application file for complete search history.

(56) References Cited

U.S. PATENT DOCUMENTS

| | | | | |
|---|---|---|---|---|
| 2,655,301 | A * | 10/1953 | Riemer | B65B 1/28 141/93 |
| 4,693,371 | A * | 9/1987 | Malpass | B65D 1/36 206/534 |
| 4,717,042 | A * | 1/1988 | McLaughlin | A61J 7/0481 221/15 |
| 6,208,911 | B1 * | 3/2001 | Yamaoka | G07F 17/0092 700/242 |
| 6,457,611 | B1 * | 10/2002 | Koehler | G07F 17/0092 141/243 |
| 6,779,663 | B1 * | 8/2004 | Pocsi | A61J 1/03 141/242 |
| 8,193,918 | B1 * | 6/2012 | Shavelsky | A61J 7/04 340/309.16 |
| 2009/0206100 | A1 * | 8/2009 | Mazur | A61J 1/03 221/1 |

(Continued)

*Primary Examiner* — Michael Collins

(57) ABSTRACT

One aspect of this disclosure provides a medication fulfillment canister. In one embodiment, the canister comprises a bottom section having a tray portion for receiving a medication therein. An upper dispensing compartment is located over a rearward end of the bottom section that is removably attached to the bottom section. A lower edge of the upper dispensing compartment is located above the bottom section to form an opening therebetween to allow a medication to pass therethrough and into the tray portion. A tray lid is removably attached to the canister and configured to cover the tray portion and rotate between an open position and a closed position. A lock is located within a wall of the bottom section that locks the tray lid in the closed position.

17 Claims, 15 Drawing Sheets

(56) References Cited

U.S. PATENT DOCUMENTS

| | | | | |
|---|---|---|---|---|
| 2013/0002795 A1* | 1/2013 | Shavelsky | ............... | A61J 7/04 |
| | | | | 348/14.01 |
| 2013/0030566 A1* | 1/2013 | Shavelsky | ............... | A61J 7/04 |
| | | | | 700/244 |
| 2014/0094966 A1* | 4/2014 | Savage | ................. | B25H 3/00 |
| | | | | 700/237 |

* cited by examiner

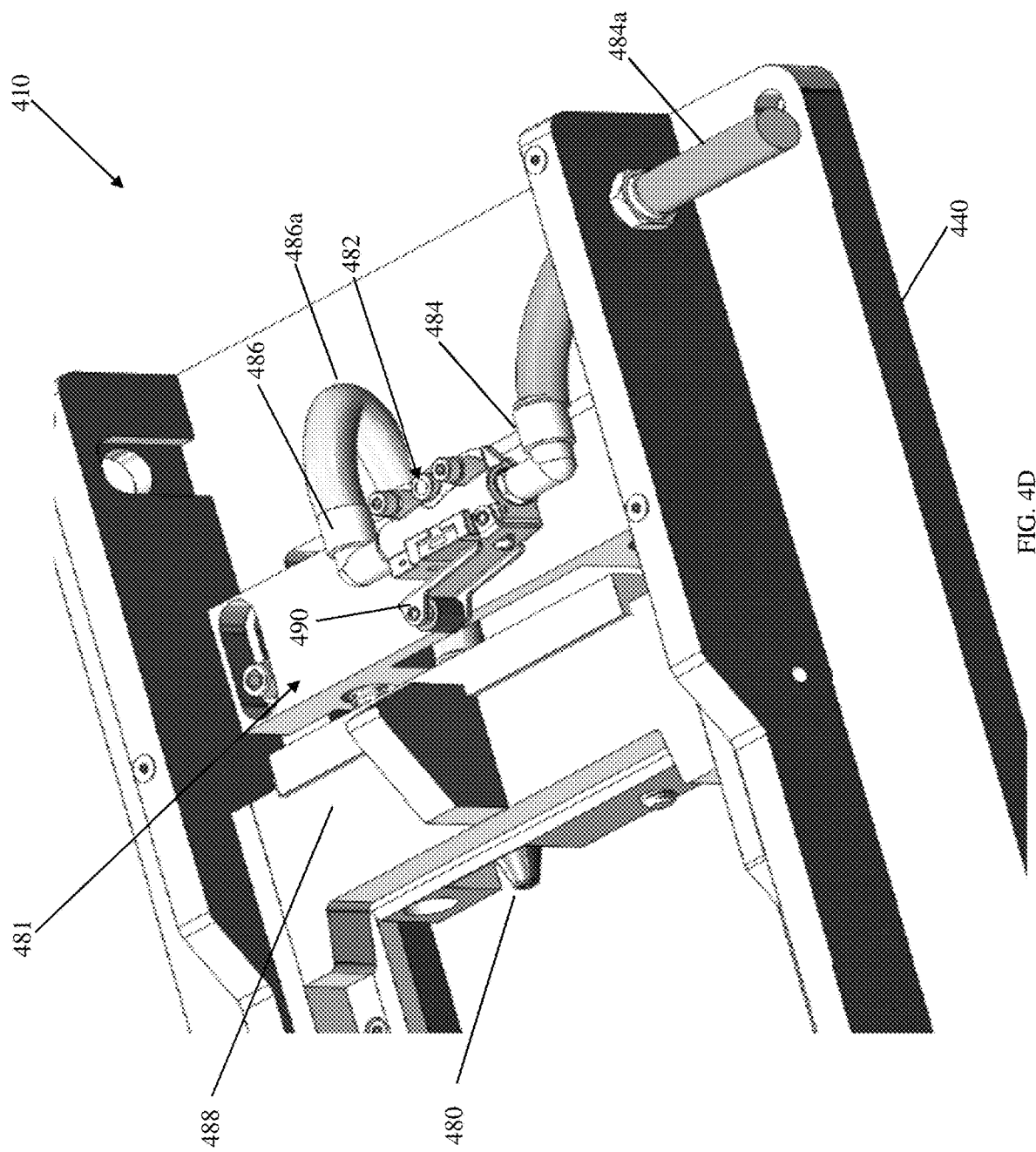

SECURE PORTABLE PILL CANISTER FOR ORDER FULFILLMENT

CROSS-REFERENCE TO RELATED APPLICATION

This application claims the benefit of U.S. Provisional Application Ser. No. 62/192,276, filed by Michael J. Doke, et al. on Jul. 14, 2015, entitled "SECURE PORTABLE PILL CANISTER FOR ORDER FUFILLMENT," commonly assigned with this application and incorporated herein by reference.

TECHNICAL FIELD

This application is directed to a secure pill canister for order fulfillment and a process for using the secure canister during order fulfillment, including a disassembly rack and automated transportation unit.

BACKGROUND

Over the last several years, the number of people on prescription drugs has increased, and as population's median age continues to increase, the number of those on prescription drugs will mostly likely continue to increase as well. Additionally, large health care providers, such as the Veteran's Administration and similar governmental administered health care programs, have seen increased prescription needs of the patients that they serve. In view of this growing fulfillment need, large prescription service providers have arisen. With the advent of these large prescription suppliers, shipment or order fulfillment has grown significantly within the last few years to meet the public's growing prescription needs. The broad availability of internet access has allowed consumers, both large and small, to purchase prescription medicines on line, while sitting in the comfort of their own homes. To fulfill these order requests, suppliers have developed various, manual fulfillment systems in an attempt to keep pace with the growing number of consumer requests. Often times, these fulfillment systems include conveying controlled substances in unsecured containers from one fulfillment station to another. Additionally, large bulk prescription fulfillment, in general, is manually time intensive, which can lead to increased service costs and result.

SUMMARY

One aspect provides a medication fulfillment canister. In one embodiment, the canister comprises a bottom section having a tray portion for receiving a medication therein. An upper dispensing compartment is located over a rearward end of the bottom section that is removably attached to the bottom section. A lower edge of the upper dispensing compartment is located above the bottom section to form an opening therebetween to allow a medication to pass therethrough and into the tray portion. A tray lid is removably attached to the canister and configured to cover the tray portion and rotate between an open position and a closed position. A lock is located within a wall of the bottom section that locks the tray lid in the closed position.

Another aspect of this disclosure presents a canister transportation unit for automatically transporting one or more canisters to a fulfillment station. In one embodiment, the transportation unit comprises a housing having one or more transport levels located. Each level has a motor driven conveyor belt that operates to move canisters within the transportation unit. In aspect of this embodiment, each conveyor belt may have an associated scanner or camera that electronically identifies the canister and its contents. Additionally, the transportation unit comprises a microprocessor controller and accessible memory and wireless communication systems located thereon that allow the transportation unit to communicate with a master controller or independently navigate its way across a fulfillment facility to the appropriate fulfillment station upon receiving a command signal to do so.

Another aspect of this disclosure presents a disassembly rack used to disassemble a canister. In one embodiment, the disassembly rack has a base and opposing frame members secured to the base. Each of the frame members have a track that extends along and near the outer perimeter of the frame members. The tracks have one or more position notches located at their respective upper ends. This embodiment further comprises a carriage member that is slidably secured between the opposing frame members and at the lower end of the disassembly rack and is designed to hold a fulfillment canister. The carriage comprises opposing mounting blocks mounted to each inner side of the carriage. Each of the mounting blocks has mounting grooves that partially extend along an inner surface of the mounting blocks. The slots' respective lengths cause the fulfillment canister to be in a correct position within the disassembly rack when positioned within the carriage. The outer sides of the carriage include posts on opposing sides thereof that slidably engage the tracks and glide within the tracks, as the carriage is rotated from the bottom of the disassembly rack to its top.

In yet another embodiment, this disclosure provides a medication fulfillment system. This embodiment comprises a medication fulfillment canister. In one embodiment, the canister comprises a bottom section having a tray portion for receiving a medication therein. An upper dispensing compartment is located over a rearward end of the bottom section that is removably attached to the bottom section. A lower edge of the upper dispensing compartment is located above the bottom section to form an opening therebetween to allow a medication to pass therethrough and into the tray portion. A tray lid is removably attached to the canister and is configured to cover the tray portion and rotate between an open position and a closed position. A lock is located within a wall of the bottom section that locks the tray lid in the closed position. This embodiment further comprises a medication filling station that has a disassembly rack configured to hold the medication fulfillment canister in an inverted position and hold the upper dispensing compartment in an inverted position upon removal of the bottom section to receive a given medication therein. The medication filling station further comprises an air injection system including an air manifold having a gas supply end and a gas outlet end, and a biased push plate, said gas outlet end connectable to said lock of said canister. This embodiment further comprises a fulfillment station that has a vibrator station configured to receive the medication fulfillment canister therein. One or more optical scanners are coupled to a fulfillment controller for reading identification data located on the medication fulfillment canister to identify a medication located within the canister. An air push device is also provided for unlocking the canister's lock and allowing the tray lid to be placed in an open position.

Another embodiment provides a method of fulfilling a medication subscription. This embodiment comprises inverting a medication fulfillment canister to expose a removable bottom section of the medication fulfillment canister, removing the bottom section to expose a dispensing compartment, and placing a prescribed medication in the dispensing compartment. The fulfillment canister has identification data located thereon that identifies the prescribed medication. The method further comprises attaching the bottom section onto the dispensing compartment. The medication fulfillment canister has a tray portion and tray lid located thereover. The tray lid is in a closed and locked position. The medication fulfillment canister is conveyed to a fulfillment station, and the identification data is scanned with an optical scanner to verify that the correct medication is positioned within the fulfillment station. The tray lid is unlocked and opened to expose the medication located in the tray portion, and a robotic arm is used to remove a prescribed number of the medication from the tray portion and place them in a prescription bottle.

BRIEF DESCRIPTION

Reference is now made to the following descriptions taken in conjunction with the accompanying drawings, in which:

FIGS. 4A-4G illustrate a medicine supplying station and a disassembly rack that is used to disassembly and supply the canister with a target medication;

DETAILED DESCRIPTION

This disclosure describes various embodiments of a unique, portable canister, and other fulfillment apparatus that can be used in an automated medication, (e.g., capsules or tablets) fulfillment process. The canister is easily portable and can accommodate various shapes and sizes of pills, both prescription drugs and over-the-counter medications or vitamins manufactured in tablet or capsule form (hereinafter referred generically to as "medication" or "medications"). A target medication, as used herein, is one that is filled by the supplier pursuant to a particular order or prescription. Among other unique features, the canister's design allows easy disassembly for re-filling and cleaning to prevent cross-contamination between different drugs. It also includes a locking mechanism that keeps the contents secure by preventing unintended access during the fulfillment process and unauthorized removal of the fulfillment medication. This feature is particularly advantageous in those instances where the medication is a narcotic drug or other controlled substance. As provided herein, the canister's various features and designs are very useful in a fully or highly automated fulfillment system (e.g., animatronic or robotic systems), as described below.

Figure 1:
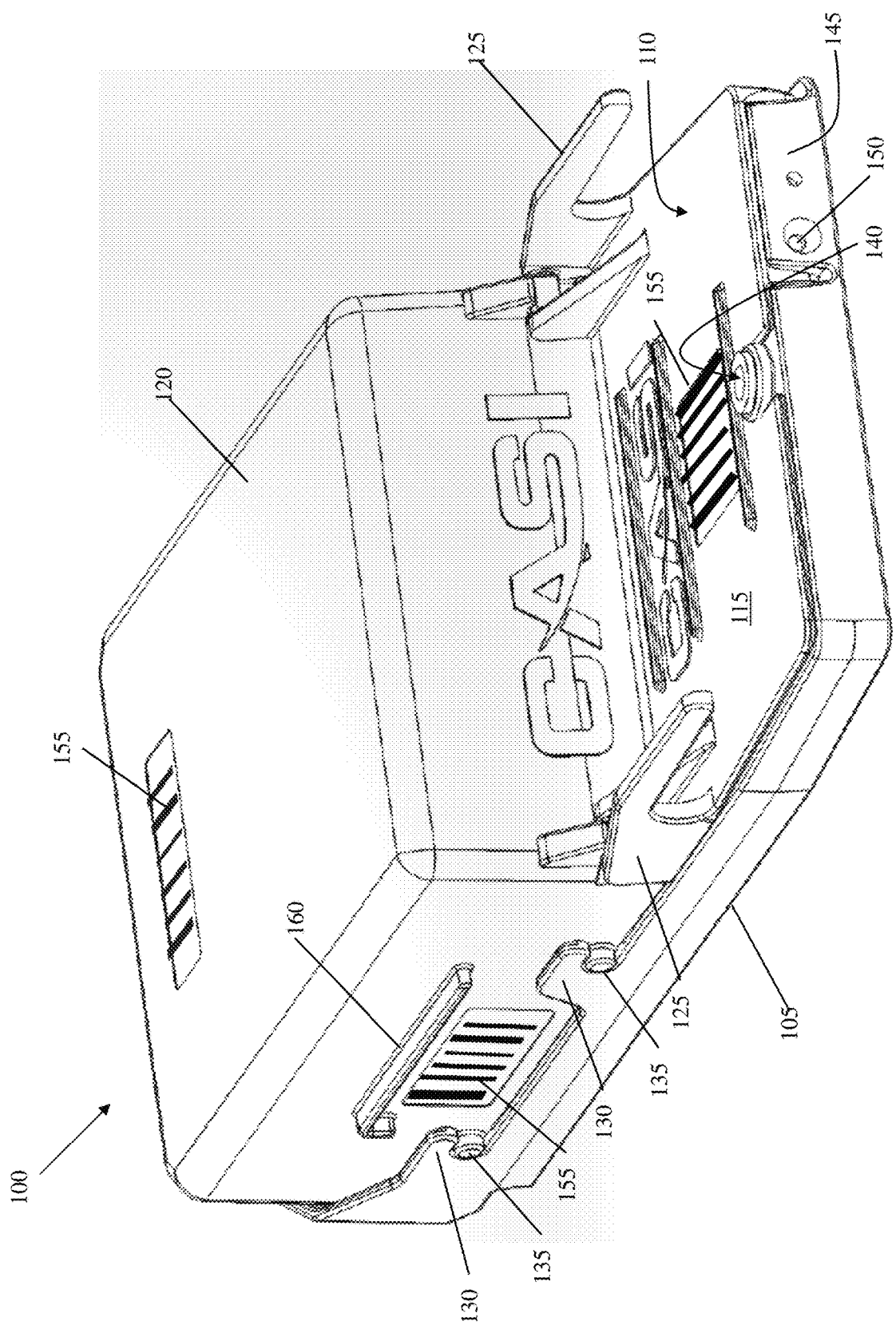
FIG. 1 illustrates a perspective view of one embodiment of the canister provided by this disclosure.

FIG. 1 illustrates one embodiment of a portable canister 100, as provided herein, that a supplier may use to fulfill a medication order in a unique, unconventional automated fulfillment system. The automated fulfillment system includes one or more fulfillment stations that use animatronics, such as robotic arms, to attach coded labels onto medication bottles or blister packs, fill the bottles or blister packs with the appropriate medication and organize grouped medication orders within the system. The overall fulfillment system comprises one or more controllers that have a sufficient number of microprocessors, memory, communication circuitry, and software algorithms associated therewith to provide instructional commands to the various fulfillment apparatus. The one or more controllers may communicate, wirelessly or by hard wire, with one or more sub-controllers located at each given fulfillment station, or it may communicate with sub-controllers associated with individual pieces of equipment that are used in the automated fulfillment system. Alternatively, a number of individual controllers may cooperatively communicate, wirelessly or by hard wire, with each other to direct the various functions of the fulfillment system.

In the illustrated embodiment of FIG. 1, the canister 100 includes a bottom 105 that has a front tray portion 110 covered by a removable tray lid 115. An upper dispensing compartment 120 is located over a rearward or back end of the bottom 105 and stores medication during the fulfillment process. The dispensing compartment 120 is slidably engaged with the bottom 105, and when the tray lid 115 is in a closed position, the tray lid 115 prevents the dispensing compartment 120 from moving forward and becoming detached from the bottom 105. In one embodiment, the tray portion 110 has sufficient translucency or transparency to allow light to pass through from its underside, which illuminates essentially back-lights the medication sufficiently such that an optical device, such as a camera or other optical scanner, can determine the correct shape and physical condition of the medication.

In one embodiment, the tray lid 115 includes one or more lifting surfaces 125 that allow a robotic arm to lift the tray lid 115 to uncover the tray portion 110, thereby allowing access to the medication. In the illustrated embodiment, the lifting surfaces 125 are cantilevered lifting arms. The lifting surface 125 configuration(s) may vary, but present a surface sufficient for a robotic arm to engage and lift the tray lid 115 to an open position. The canister 100 has a configuration (i.e. design) that allows for easy disassembly. For example, the bottom 105 may include one or more notches 130 configured or designed to receive a corresponding post 135 formed in the dispensing compartment 120. The notches 130 and posts 135 may be on one or both sides of the canister 100. In other embodiments, these features may be reversed with respect to the bottom 105 and dispensing compartment 120. When the tray lid 115 is closed and in place, it prevents forward movement of the dispensing compartment 120. However, when the tray lid 115 is removed, the dispensing compartment 120 can move freely forward, allowing the posts 135 to disengage from the notches 130 and the removal of the dispensing compartment 120 from the base 105. It should be understood that the foregoing is but one example of a coupling mechanism that could be used to provide a canister that can easily be disassembled and that other coupling configurations would be apparent to those skilled in the art, given the disclosure herein. It should be understood that the geometric dimensions, both size and shape, of the illustrated embodiment may vary, depending on the amount of medication that dispenses from the canister 100.

As explained in more detail below, in one embodiment, the canister 100 may include an accompanying pick-up tip 140 that seats in a pick-up tip port or opening (not shown in this view) formed in the tray lid 115 and inner ledge of the bottom 105. The size or type of pick-up tip 140 is selected based on the medication initially placed in the dispensing compartment 120. The pick-up tip 140 stays with the canister 100 during the fulfillment process so that it is accessible to be used by a robotic arm to pick up medication from the tray portion 110. Additionally, the canister 100 includes a locking mechanism (See FIG. 2 below). In one embodiment, the locking mechanism is a pneumatically actuated locking mechanism that is located in a front wall 145 of the bottom 105. A pneumatic chamber of the locking mechanism is accessible through an injection port 150 that is located in a wall 145 of the canister 100.

Additionally, the canister 100 may include identification (ID) data, such as bar code areas 155 that contain bar code data or an electronic identification chip or tag, such as a radio frequency identification (RFID) tag, located thereon that allow the fulfillment systems controller to identify and track the canister 100 through various stages of the fulfillment process. When a bar code is used, it may be any known type of bar code, for example, it may be a straight-line bar code, as schematically shown in FIG. 1, or it may be a design code, such as an Aztec Code, a CrontoSign code, a Data Matrix code or a SPARQCode, to name just a few. In those embodiments that use an RFID tag or other known electronic identification technology, the electronic identification tag or chip may attach to the canister's 100 surface or be embedded within the canister 100.

The ID data associates a given canister 100 with a particular medication, and a controller stores this data in the fulfillment systems memory. The fulfillment system's controller(s) then use this ID data to identify the type of medication located within the dispensing compartment 120. When the canister 100 is positioned in its proper fulfillment station, a scanner reads the ID data to confirm the type of medication by cross-referencing the stored data in the fulfillment system's database. As explained below, the fulfillment system's controller(s) use this ID data to crosscheck the medication that dispenses from the dispensing compartment 120 during the fulfillment process. In certain embodiments, the canister 100 also includes a mounting rail 160 located on one or opposing sides of the dispensing compartment 120 that allows the mounting of the dispensing compartment 120 onto a disassembly rack. A manual operator or an automated robot uses the disassembly rack to disassemble the canister 100 and place the correct type and amount of target medication in the dispensing compartment 120.

Figure 2:
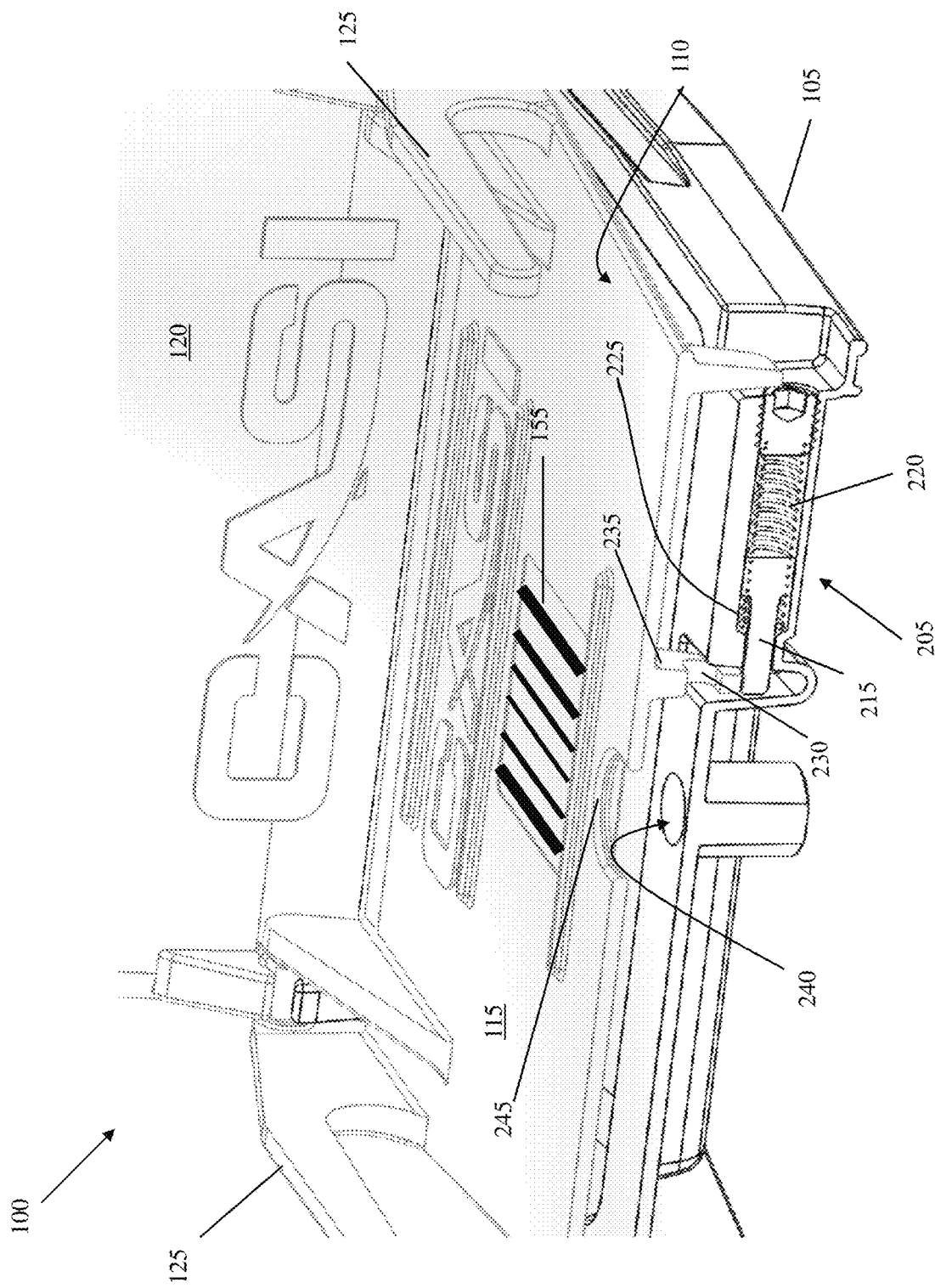
FIG. 2 illustrates an enlarged view of a locking mechanism included in the canister of FIG. 1.

FIG. 2 is an enlarged view of a portion of the canister 100 showing more details of one embodiment of a locking mechanism 205 incorporated into the structure of the canister 100 that secures the medication within the canister 100 to prevent unauthorized access during the fulfillment process. In the illustrated embodiment, the locking mechanism 205 is located in a front wall 210 of the canister 100, but in other embodiments, it may be located in a sidewall of the canister 100. In the illustrated embodiment, the locking mechanism 205 is a pneumatically operated lock that includes a pin 215 and a spring 220 that cooperatively operate within a chamber 225 located in the front wall 210. In other embodiments, however, the locking mechanism 205 may be electronic, magnetic, or a manual (lock-key) mechanism.

In the illustrated embodiment, the pin 215 is normally biased by the spring 220 in a locked position, and as such, the pin's 215 default state is a locked position. The locking mechanism 205 cooperates with a notch 230 or hole formed in a tongue 235 that extends downwardly from the tray lid 115 and cooperatively engages the pin 215 of the locking mechanism 205. When the canister 100 arrives at the designated fulfillment station, a manual operator or animatronics device injects air or another type of gas into the chamber 225 through the injection port 150. (FIG. 1). The gas drives the pin 215 against the spring 220 and unlocks the tray lid 115, which allows it to open to provide access to the tray portion 110. Once the gas pressure dissipates, the spring 220 biases the pin 215 back into a lock position, as shown in FIG. 2. Those skilled in the art, given the teachings presented herein, will understand that the design, location, and type of locking mechanism may vary from the embodiments presented herein and that these alternative embodiments are also within the scope of this disclosure.

FIG. 2 also illustrates the pick-up tip port 240 formed in the canister's 100 ledge in which the appropriately assigned pick-up tip 140 seats, during the fulfillment process. Additionally, this view illustrates a pick-up tip notch 245 formed in the tray lid 115 that allows the pick-up tip 140 to seat further within the pick-up tip port 240.

Figure 3:
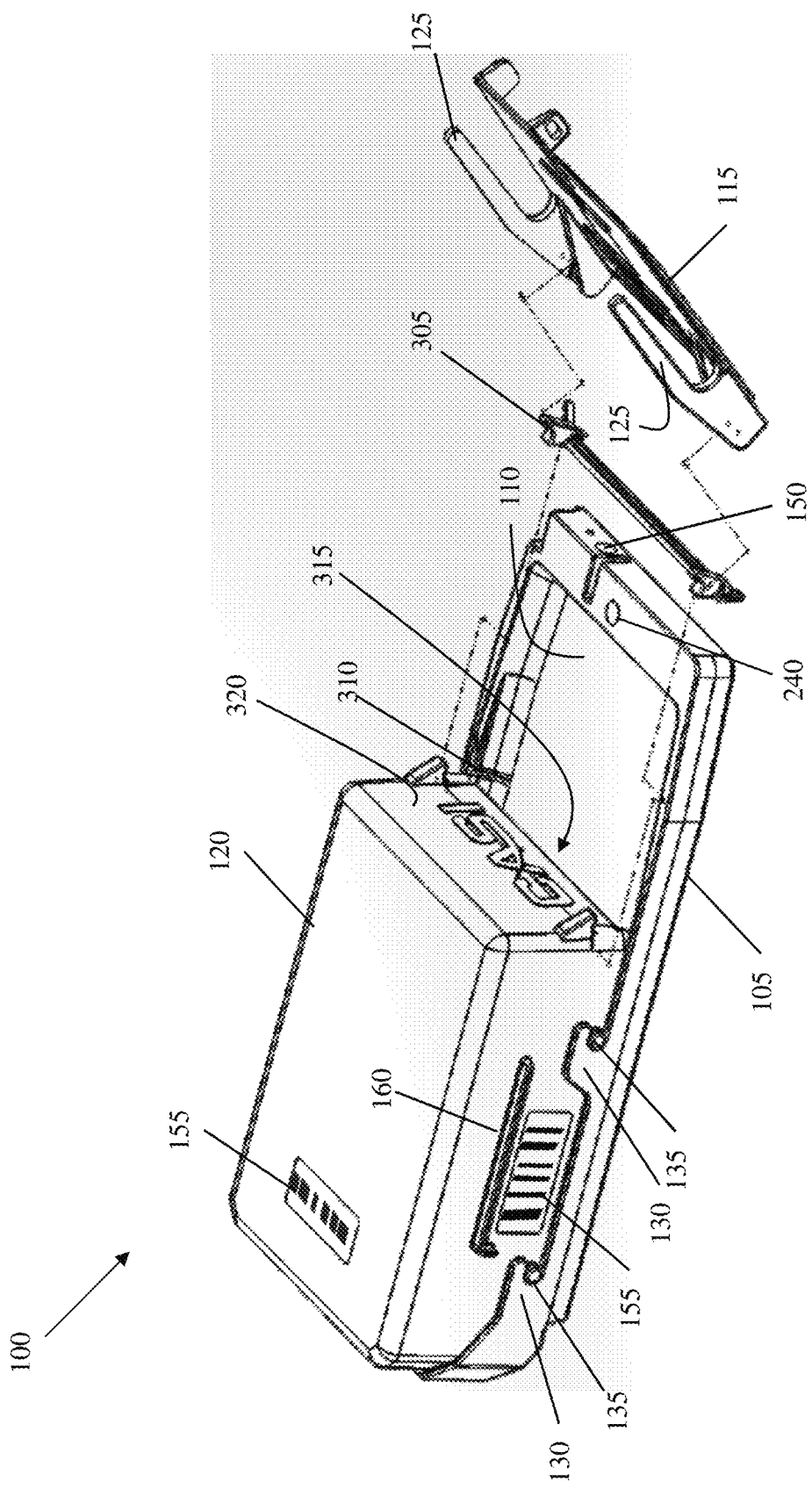
FIG. 3 illustrates an exploded view of the canister of FIG. 1 that shows how the tray lid and feeding guide are removable from the canister.

FIG. 3 illustrates a partial, exploded view of the canister 100 that shows an optional feeding gate 305 and its positional location (indicated by the dashed lines) in relation to the dispending compartment 120. The feeding gate 305 removably engages slots 310 that are located on opposing sides of the bottom 105 and allows easy removal of the feeding gate 305 from the canister 100. The feeding gate 305 design or configuration may have different dimensions to accommodate different types or sizes of medication contained within the dispensing container 120. When positioned within the canister's 100 structure, the feeding gate 305 reduces an opening 315 located between the tray portion 110 of the canister's bottom 105 and a side wall 320 of the dispensing compartment 120 that extends downwardly and towards the tray portion 110. The size of the feeding gate 305 reduces the opening 315 to allow an even flow of a particular type or size of medication from the dispending compartment 120 to the tray portion 110. In other embodiments, the feeding gate 305 is not present, and in such embodiments, the physical dimensions of the opening 315 provide an even flow of medication from the dispensing compartment 120. The easy removal of the feeding gate 305 allows the interchangeability of feeding gates of different sizes to accommodate different types or sizes of medication. Additionally, in one embodiment, the cooperative engagement of the feeding gate 305 with the tray lid 115 functions to move the tray lid 115 to a partial open position when the tray lid 115 is unlocked. Alternatively, the canister 100 may include a spring or other biasing mechanism to place the tray lid 115 in an open position when it is unlocked.

Figure 4A:
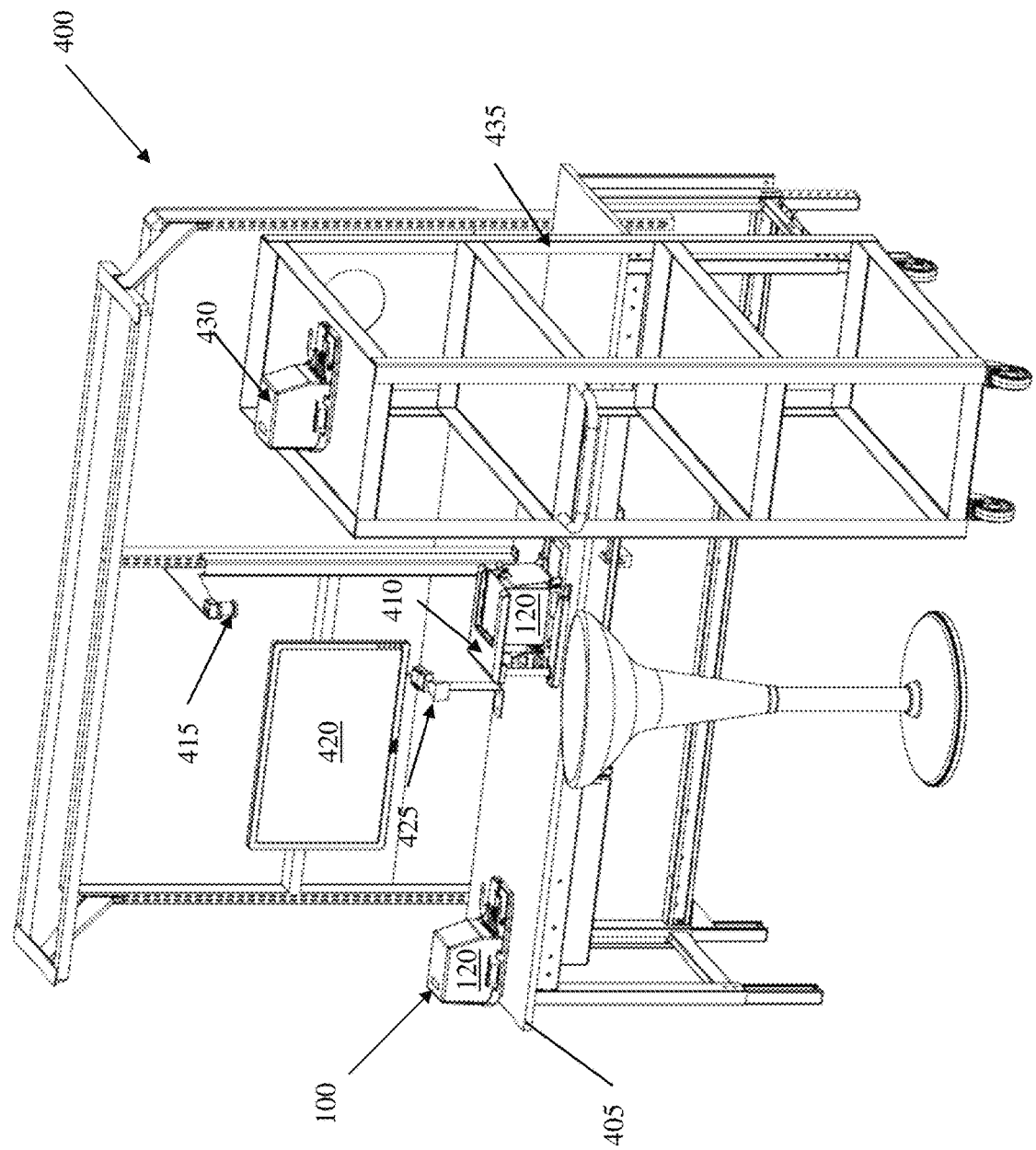

FIG. 4A illustrates one embodiment of a filling station that can be used to supply the canister 100 with the target medication. Empty canisters 100 are placed on a workbench 405, after which the canister 100 is disassembled by placing the canister 100 in a disassembly rack 410, which is designed to hold the dispensing compartment 120 (FIG. 1) in place while the bottom 105 (FIG. 1) is removed. The removal of the bottom 105 exposes the interior of the dispensing compartment 120, which allows the placement of the correct type and number of the target medication in the dispensing compartment 120. A manual operator or animatronic device supplies the dispensing compartment 120 with the correct type and amount of target medication from a main supply source (not shown). The fulfillment system's controller(s) identifies the supply source medication that has ID data that matches the canister's 100 ID data and associates that identified medication with the canister 100 using their respective ID data. A screen 420 may also display the data relating to the amount and type of medication placed into the container. Additionally, a scanner 425, such as an optical scanner, may be present in the filling station 400. The scanner 425 may scan the target medication supply ID data and input it into a database for crosscheck and reference to the correct canister 100, during the fulfillment process.

Additionally, the above-mentioned ID data 155, which identify the medication placed in the canister 100, are applied to the canister 100 so that the controller(s) can use other scanners to determine that the canister 100, and therefore the target medication, is correct for a given fulfillment station. As the dispensing compartment 120 is supplied with the target medication, a camera 415 may be present for remote viewing of the filling process by a pharmacist that can confirm that the amount and type of the target medication are correct. When the dispensing compartment 120 is supplied with the proper amount and type of medication, an animatronic device or manual operator places the bottom 120 back onto the dispensing compartment 120, using the disassembly rack 410, locks the tray lid 115 in the closed position, and places the supplied canister 430 onto a holding rack 435. A manual operator or automated conveyance system may place the supplied canister 430 in the appropriate fulfillment station.

Figure 4B:
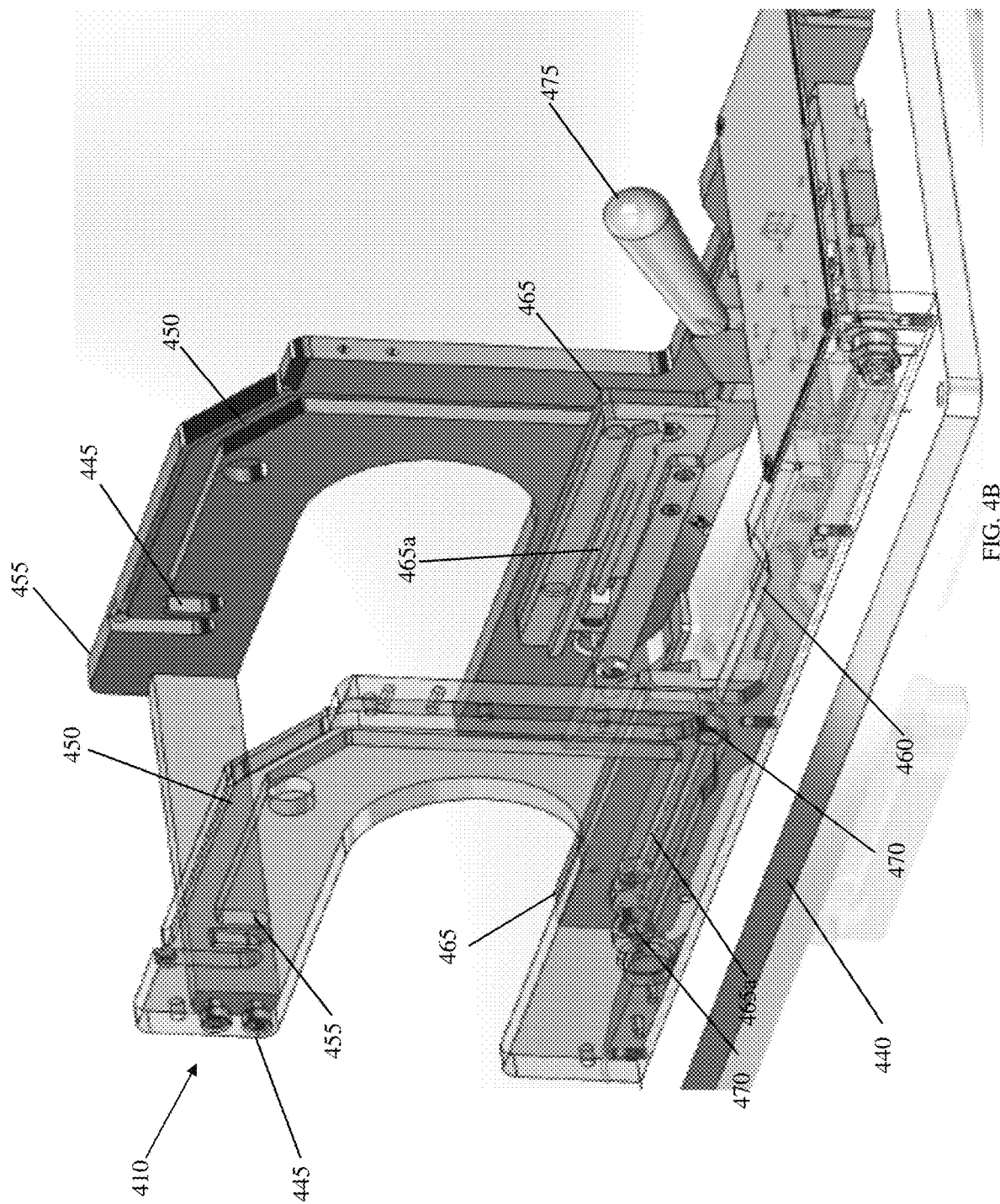

FIG. 4B illustrates one embodiment of the disassembly rack 410. In this embodiment, the disassembly rack 410 has a base 440. Opposing frame members 445 are secured to the base 440. Each of the frame members 445 have a track 450 that extends along and near the outer perimeter of the frame members 445. In the illustrated embodiment, the frame members 445 and the tracks 450 generally have a "U-shaped" configuration, however, the disclosure is not limited to this particular configuration, as other geometric configuration are also within the scope of this disclosure. The tracks 450 have one or more position notches 455 located at their respective upper ends. A carriage member 460 is slidably secured between the opposing frame members 445 and at the lower end of the disassembly rack 410 and is configured/designed to hold the canister 100 therein. The carriage's 460 configuration accommodates different sizes of canisters 100. The carriage 460 comprises opposing mounting blocks 465 mounted to the carriage's frame 460 that each have mounting grooves 465a that partially extend along an inner surface of the mounting blocks 465. The slots' 465a respective lengths cause the canister 100 to be correctly positioned within the disassembly rack 210, when placed therein. The outer sides of the carriage 460 include posts 470 on opposing sides thereof that slidably engage the tracks 450 and glide within the tracks 450, as the carriage 460 is rotated from the bottom of the disassembly rack 410 to its top, during operation. A handle 475 may also be present to provide a manual operator or animatronics device with a surface that can be easily gripped or otherwise engaged.

Figure 4C:
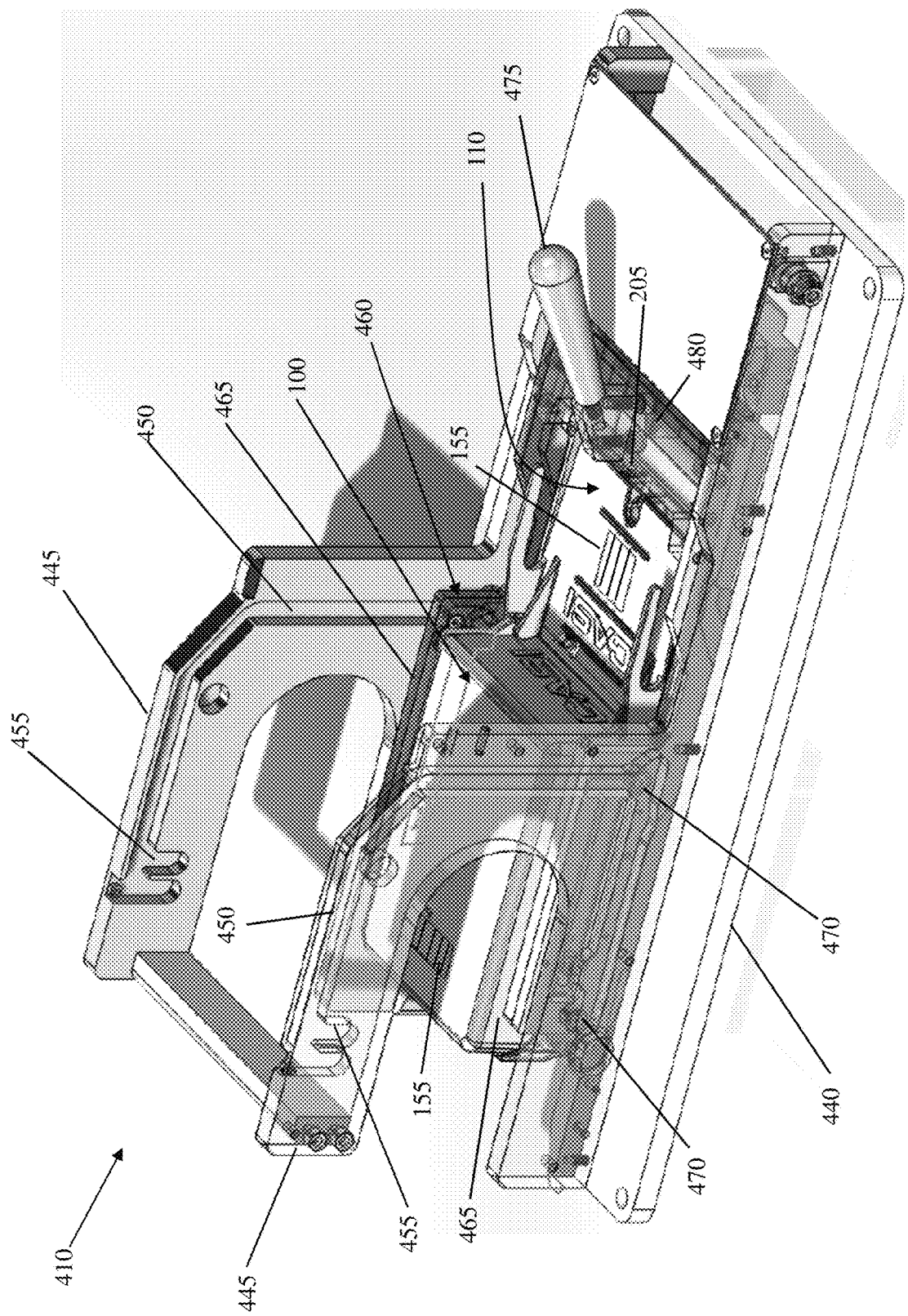

FIG. 4C illustrates the disassembly rack 410 of FIG. 4B with the canister 100 positioned within the disassembly rack's 410 frame. In certain embodiments, the disassembly rack 410 may include an air-push nozzle 480 that can be used to inject air into the locking mechanism 205 and unlock the tray lid 115. In other embodiments, the air or gas is injected into the locking mechanism 205 with a nozzle that is separate from the disassembly rack 410.

Details of one embodiment of an air injection system 481 is shown in FIG. 4D, which is an enlarged view of the injection end of the disassembly rack 410. The air injection system 481 includes an air manifold 482, which may be of conventional design, that has a gas supply end 484 and a gas outlet end 486. The gas supply end 484 is connectable to a gas supply (not shown) and the gas outlet end 486 connects to the air-push nozzle 480 by tubing 484a, 486a, respectively. The air injection system 481 further includes a biased push plate 488 that is attached to an actuator arm 490 of the release valve (not shown) of the air manifold 482. In one embodiment, the push plate 488 may be biased by a spring. When the canister 100 is placed in the disassembly rack 410, the injection port 150 is correctly aligned with the air-push nozzle 480. As the canister 100 is moved forward from this initial position, the front end of the canister 100 pushes against the push plate 488 causing the push plate 488 to push against the actuator arm 490. This actuates a release vale within the air manifold 482 that injects the air or gas into the locking mechanism chamber 205, thereby, moving the pin 215 (FIG. 2) to an unlocked position and allowing the tray lid 115 to open. This process is repeatable to lock the tray lid 115 when the supply process is completed. This is done because the pin's 215 (FIG. 2) default position is a locked position, even when the tray lid 115 is open. Thus, to close or lock the tray lid 115, gas is injected into the locking mechanism 205 to move the pin 215 to an unlocked position. Once the tray lid 115 is closed, the canister 100 is pushed away from the push plate 488, which deactivates the air manifold 482 and allows the pin 215 to move to a locked position.

It should be understood that the air injection system 481 is but one way to inject air or gas into the canister's 100 locking chamber 225 (FIG. 2) and that other mechanical or electrical or electro-mechanical systems may be used in place of the above-described embodiment.

Figure 4E:
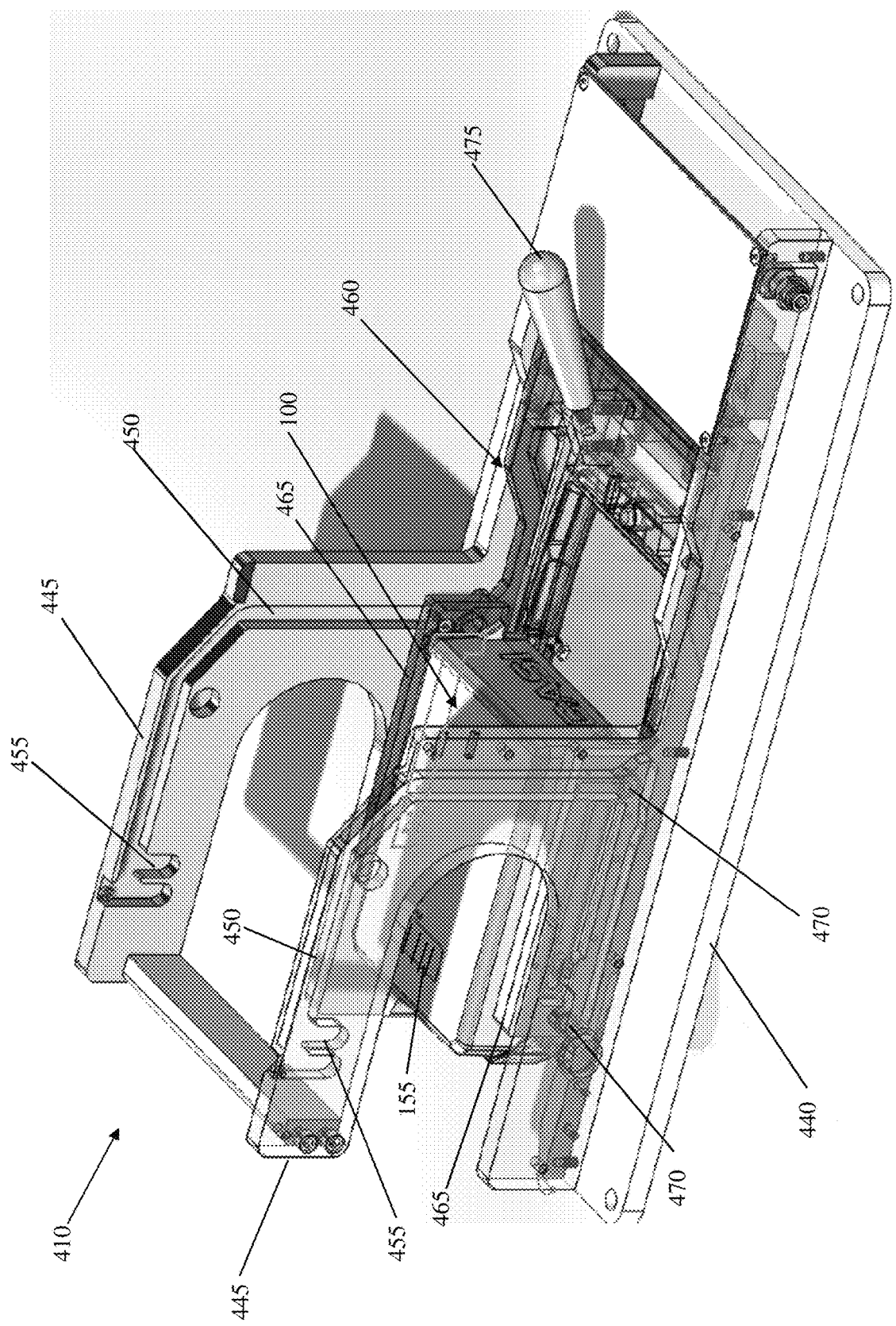
Figure 4F:
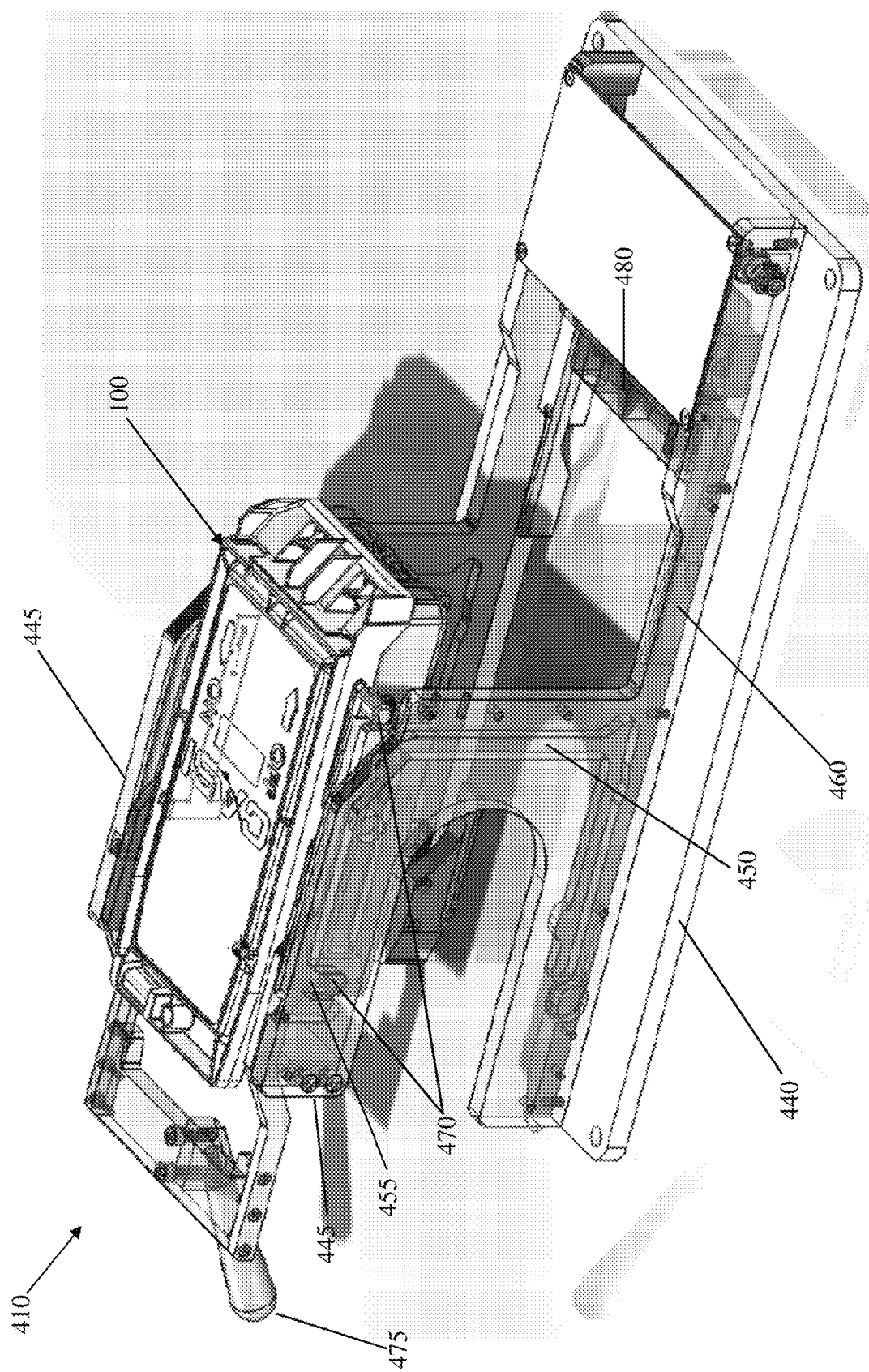
Figure 4G:
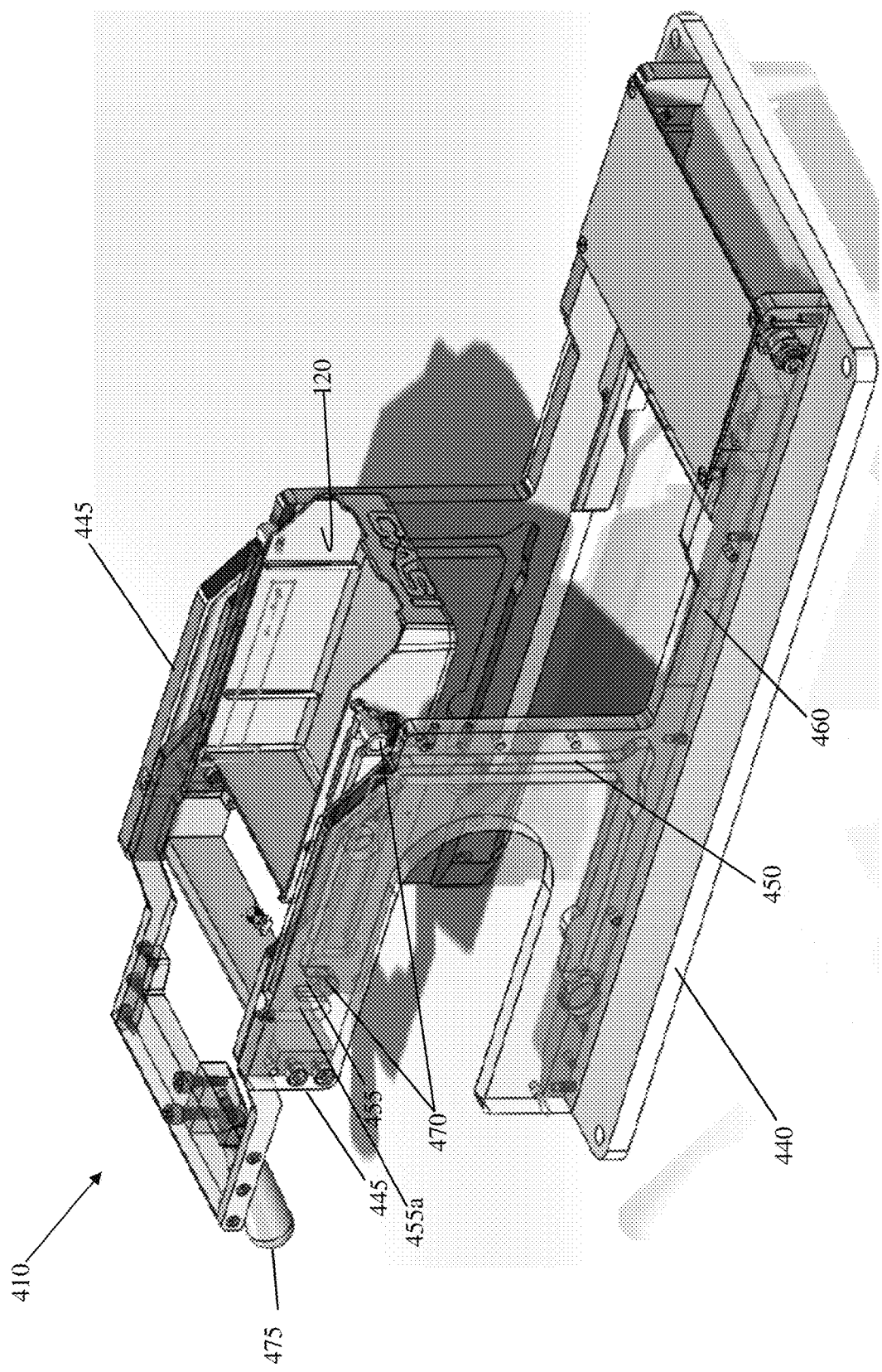

FIG. 4E illustrates the disassembly rack 410 of FIG. 4C after the removal of the tray lid 115 and FIG. 4F illustrates the disassembly rack 410 of FIG. 4E after the carriage 460 has been moved into a disassembly orientation at the top of the disassembly rack 410. To achieve this position, an animatronic device or manual operator lifts the carriage 460 and rotates the carriage 460 and canister 100 along the tracks 450 until the posts 470 engage the first position slot 455 at the top of the disassembly device 410, as seen in FIG. 4F. With the tray lid 115 removed, the base 105 of the canister 100 can be slid backward (away from the handle 475) to remove the base 105 from the dispensing compartment 120, thereby exposing the interior of the dispensing compartment 120. To remove the dispensing compartment 120 from the disassembly rack 410, the handle end of the carriage is lifted and the posts 470 are moved from position slot 455 to a second, adjacent slot 455a. Once the dispensing canister 120 is properly filled, the filled dispensing compartment 120 is placed back onto the carriage 460 located at the top of the disassembly rack 410. The posts and carriage 460 are moved from slot 455a to slot 455, after which the base 105 (FIG. 1) is placed back onto the dispensing canister 120, and the carriage 460 and canister 100 are rotated back to the lower end of the disassembly rack 410. Additionally, the proper pick-up tip 140 (FIG. 1) is placed into the pick-up tip opening. As discussed above, the pick-up tip 140 selection is based on the type of medication within the dispensing compartment 120. The feeding gate 305 and tray lid 115 (FIG. 3) are placed back onto the canister 100, and the tray lid 115 is locked in a closed position using the above-discussed air injection system.

Figure 5A:
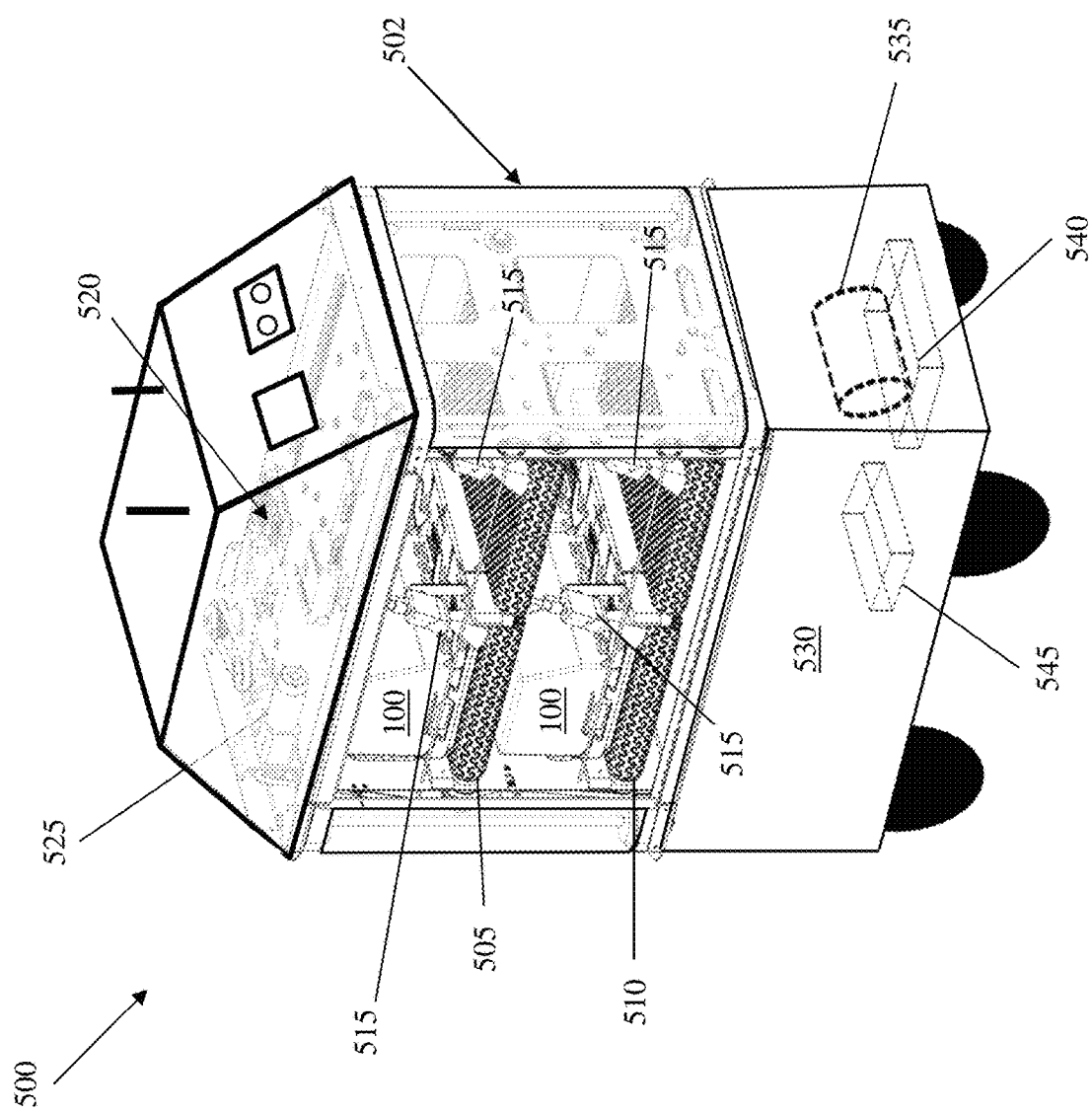
FIG. 5A illustrates an automated transport unit that can be used to transport a canister to a fulfillment station.
Figure 5B:
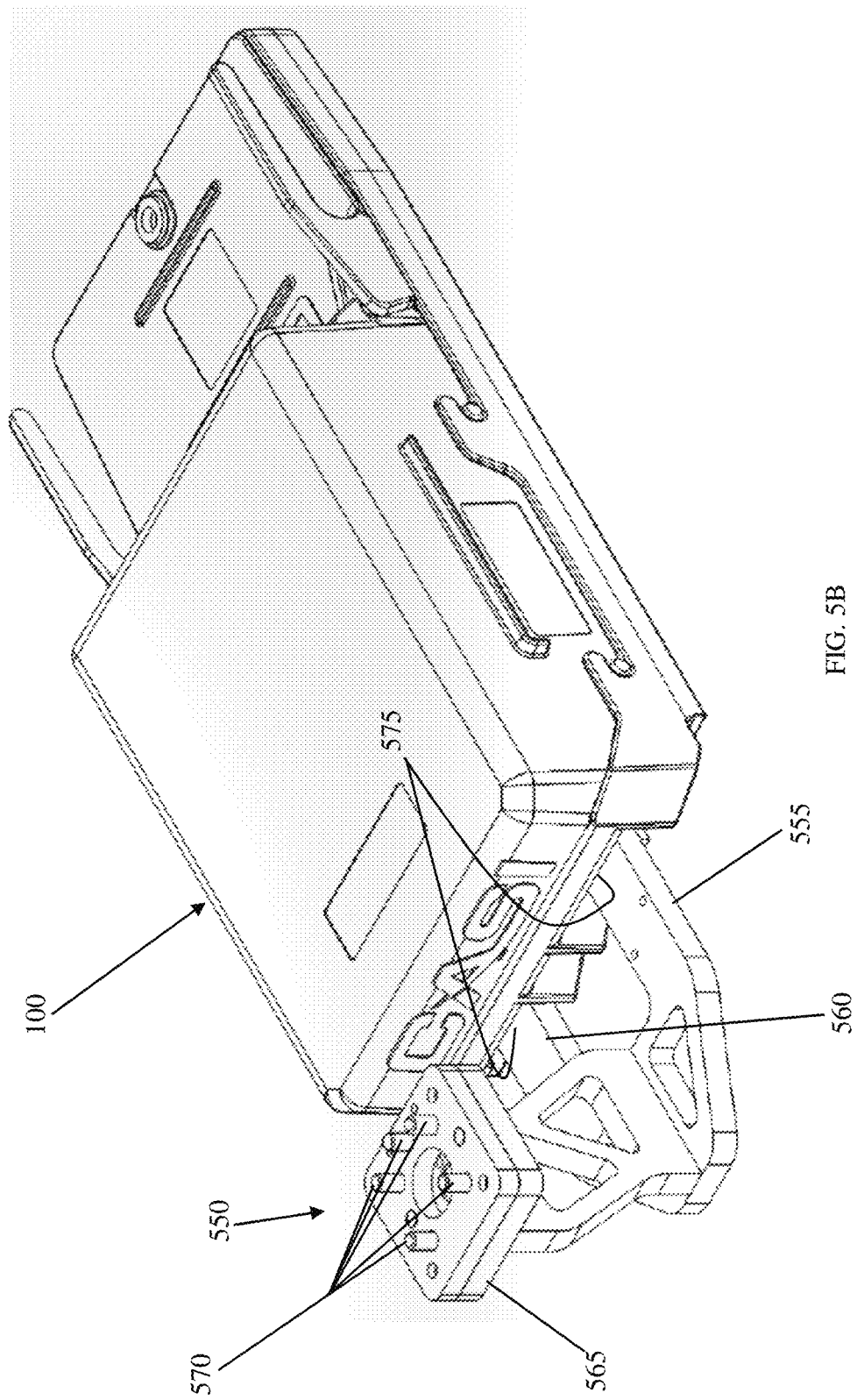
FIG. 5B illustrates one embodiment of a lifting arm that is coupable to a robotic arm that can be used to pick up the canister and place it in a fulfillment station.

FIG. 5A illustrates a unique transportation unit 500 that is part of this disclosure and that can be used to robotically transport the canister 100 across fulfillment facilities and to a designated fulfillment station. In one embodiment, the transportation unit 500 comprises a housing 502 having one or more transport levels located therein. The one or more transport levels have motor driven conveyor belts 505, 510 that operate to move canister's 100 within the transportation unit 500. In the illustrated embodiment, the transportation unit 500 holds four canisters 100, but other configurations may be designed to hold more or less than four. When the canister 100 is supplied with the target medication as described above, the canisters 100 can be manually or robotically placed in and removed from the transportation unit 500. Each conveyor belt 505, 510 may have a scanner or camera 515 associated therewith that scans the above-discussed ID data to identify the canister 100 and its contents. The controller(s) can then use the scanned data to coordinate other fulfillment processing steps.

The transportation unit 500 is a "smart" unit in that it has a microprocessor controller and accessible memory and wireless communication systems 520 located thereon. This smart system allows the transportation unit 500 to communicate with one or more controllers that control the fulfillment system to navigate its way across a fulfillment facility to the appropriate fulfillment station upon receiving a command signal to do so, or allow it to navigate independently. The hardware of the controller and wireless communication systems 520 may be of conventional design. However, the controller 520 is coded with unconventional navigation and instructional software programming algorithms that allow the transportation unit 500 to convey itself to the appropriate location, appropriately operate the conveyor belts 505 and 510, and communicate with other fulfillment controller(s) that control various aspects of the overall fulfillment process.

Additionally, the controller system 520 also controls the operation of a motor 525 that is operatively coupled to the conveyor belts 505, 510 to move the canister's 100 within and out of the transportation unit 500.

Located below the conveyor level, a driving compartment 530 houses an electrical driving motor 535 and a steering mechanism 540 both of which are operatively coupled to the wheels. Since the electrical driving motor and steering mechanism may be of conventional design and function, they are shown only generically are not described in detail. The electrical motor is electrically coupled to a battery 545, and both the motor 535 and steering mechanism 540 are operatively coupled to the controller 520 that controls the operation of the motor 535 and steering mechanism 540. The controller sends signals to the electric motor 535 and steering mechanism 540, both of which may have their own respective sub-controllers that communicate with controller 520, to cause the transportation unit 500 to be directed to the appropriate location upon receiving a command signal that includes destination coordinates within the fulfillment facility.

Once the controller properly identifies and verifies the canister 100 and its target medication, a manual operator or animatronic places each canister 100 into a separate bay. The transportation unit 500 proceeds across the fulfillment facility to a filling station where the canisters 100 are automatically or manually removed from the transportation unit 500.

In one embodiment, the automated transportation unit 500 may have an open configuration as shown in FIG. 5A. However, in other embodiments, the transportation unit 500 may be enclosed to secure the contents within it. For example, the transportation unit may have a belt with a window or aperture formed therein that can be driven by a motor to rotate the belt within an interior of the transportation unit 500. Thus, when there is a need to place a canister 100 within the transportation unit 500, a motor will rotate the belt to cause the opening to be placed in the location that is need for interior access. After the canister(s) 100 is/are placed within the transportation unit 500, the motor will rotate the belt so that the window or aperture is moved to an inaccessible position within the transportation unit 500, thereby securing the contents therein. In one embodiment, the belt is a conventional conveyor belt material, such as leather, polyethylene (PE), polypropylene (PP) and polyacetal (POM). The belt may have a modular design to allow a user to tailor the dimensions, such as length and width, of the belt as needed. Those in the industry that use such materials know of these modular belt systems and materials. Additionally, the belt motor may be operated either manually or by a controller that will position the access window in the correct position during the fulfillment process to keep the contents as secure as possible. This is particularly desired when the medication within the canister 100 is a controlled substance.

Figure 6:
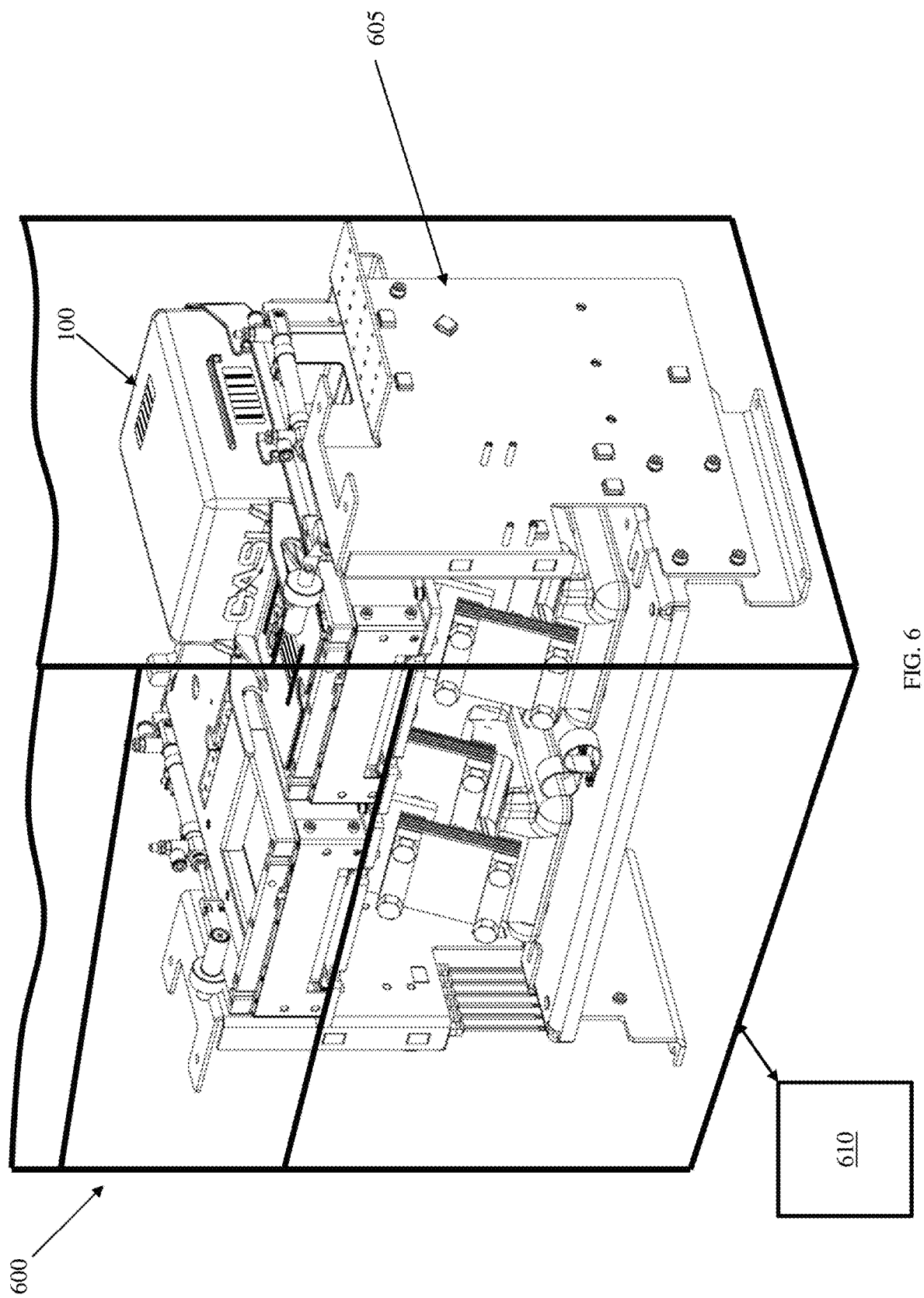
FIG. 6 illustrate one embodiment of a fulfillment station as provided by this disclosure.

When the canister 100 is filled, and the target medication's identification and quantity are verified, the canister 100 is moved to a fulfillment station 600, as generally illustrated in FIG. 6. In one embodiment, a lifting arm 550 that is coupable to a robotic arm (not shown) is used to place the canister 100 into the fulfillment station 600. In the illustrated embodiment, the lifting arm 550 has two spaced apart tines 555 and 560 that are attached to a coupling head 565 that has coupling posts 570 that allow the lifting arm 550 to be coupled to a robotic arm. The canister 100 has a pick space 575 located underneath that allow the tines 555, 560 to be inserted under the canister 100.

In one embodiment, the fulfillment station 600 is a cabinet that includes a vibrator station 605, which may be of conventional design, and includes the appropriate communication circuitry, and in some instances its own controller, that communicates with the fulfillment system's controller(s) 610 so that the fulfillment station 600 can receive various fulfillment commands from the fulfillment system's controller(s). Though some fulfillment systems may employ only one such fulfillment station 600, a typical fulfillment system will employ multiple units that are joined together by a conveyor belt system that runs through the multiple fulfillment stations 600, such that a target medicine bottle or blister pack can traverse from fulfillment station 600 to another.

In addition, the fulfillment station 600 includes optical scanners and one or more robotic arms, which are not shown and one or more canister bays that hold the individual canisters 100. A robotic arm removes the canister 100 directly from the transportation unit 500 or from a storage bay positioned adjacent the fulfillment station 600 and into an assigned station on the vibrator 605. The canister 100 is then scanned, or read in the case where a RFID tag is used, for identification, and the fulfillment's controller(s) store the data, so that the controller(s) knows the canister's 100 location and its contents. In one embodiment, the fulfillment station 600 is equipped with an air-push device, similar to the one described above regarding the disassembly rack. In this application, the air-push device is used to unlock and open the canister 100 in the same manner as previously described above. This may be done robotically or manually.

Figure 7:
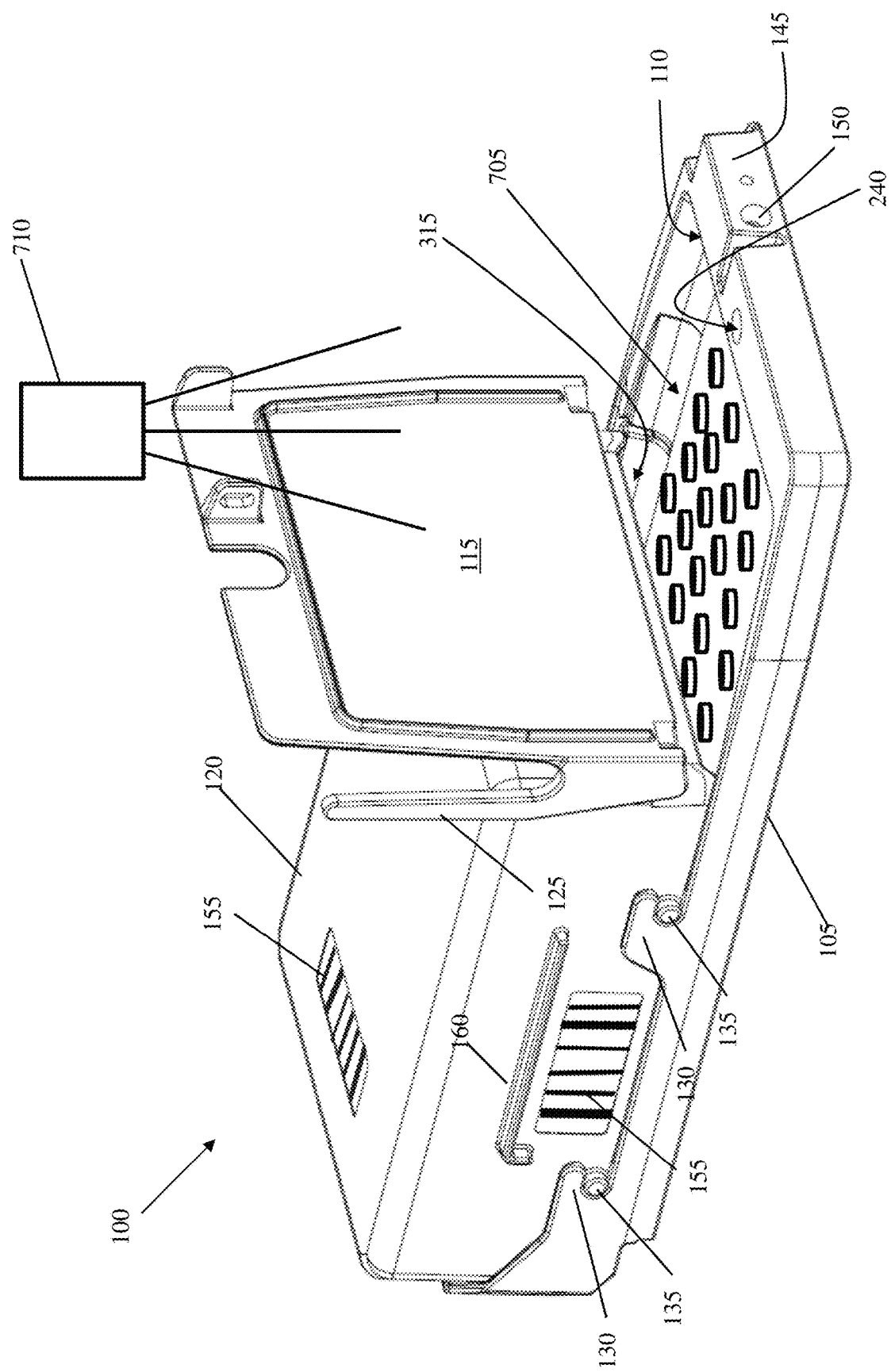
FIG. 7 illustrates medication dispensed in the tray portion of the canister when in a full open position.

When the tray lid 115 is unlocked, a robotic arm may open it to a fully open position as illustrated in FIG. 7. Though not shown in this view, it should be understood that at this stage of the process, the canister 100 is positioned within previously discussed fulfillment station 600. The fulfillment system's controller signals the vibrator unit 605 to vibrate for a prescribed time. During the vibration cycle, target medication 705 flows from the dispensing compartment 120 to the tray portion 110 through the opening 315. As previously discussed, the tray portion 110 allows light to come through from its underside, effectively backlighting the medication 705. This enhances the medication's 705 image and aides identification of the medication 705 by an optical device 710, such as a camera, that provides verification that the medication 705 is of the correct type and shape and not broken or damaged in any way. In those instances where the optical device is a camera, the image may be transmitted to a pharmacist who can further verify the type medication.

Figure 8:
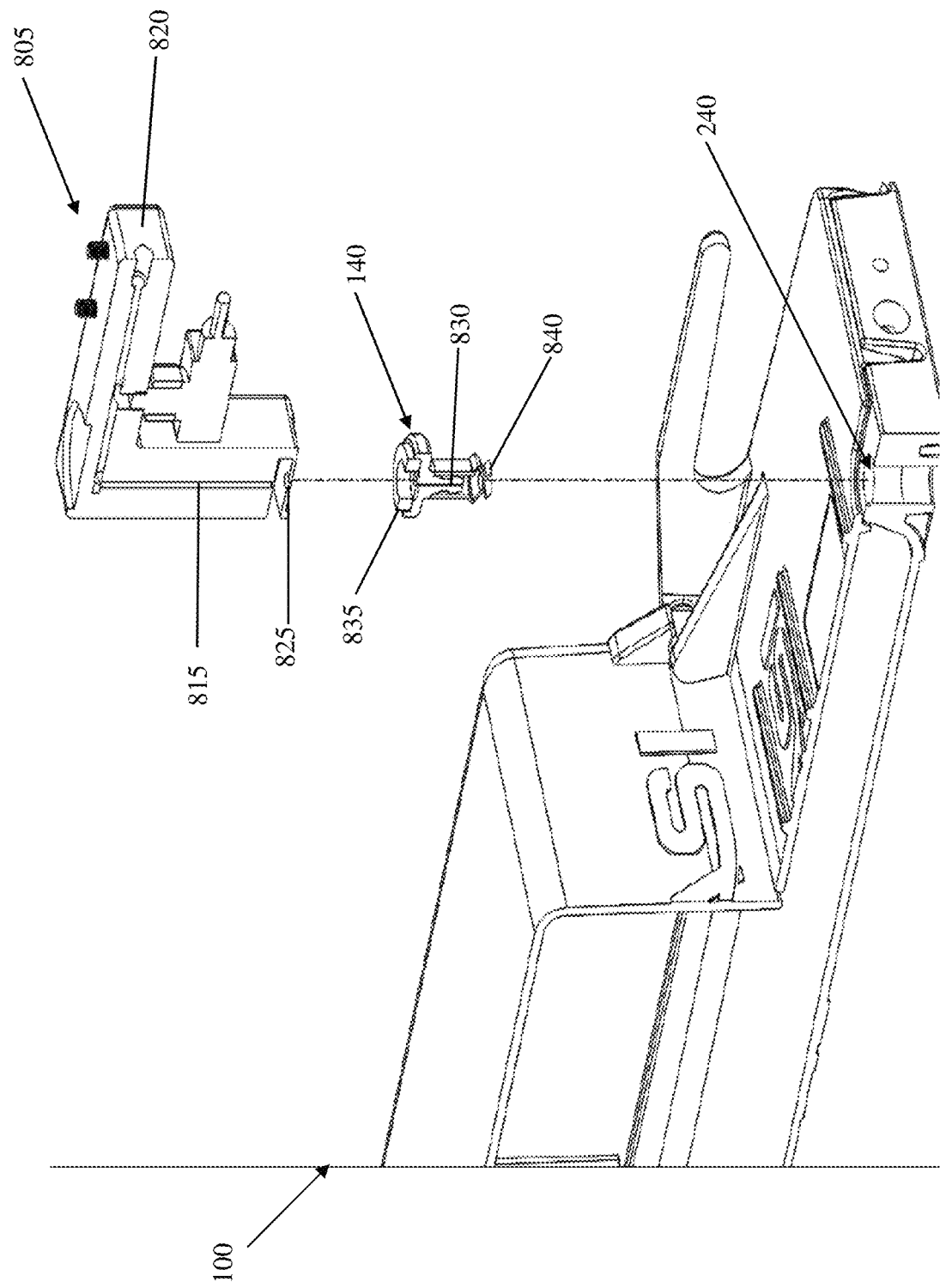
FIG. 8 illustrates an embodiment of a pick-up system and tip that can be used to pick and place a target medication in a corresponding labeled bottle.

FIG. 8 illustrates the canister 100 and associated pick-up device 805 and the accompanying pick-up tip 140, as previously discussed. The pick-up device 805 may be of conventional design, except for having an electromagnetic end, is attachable to a robotic arm that can move very quickly to pick up individual tablets or capsules and place them in a designated medicine container or bottle that is matched to the target medication.

In one embodiment, the pick-up device includes a digital air pressure sensor that provides real-time feedback to a robotic device of air pressure actually present at the pick head. With this sensor, the robotic device performs verifications that a picked product has been secured to a picking tool or that a placed product has come off of a picking tool by comparing the air pressure readings before and after the respective pick operation and place operation. Similarly, with this sensor, the robotic device also performs verifications that a fastened picking tool has been secured to the pick head or that a removed picking tool has come off of the pick head. This positive verification of picking tool interchange is an advantage of the present invention.

The pick-up device 805 has an air channel 815 that extends from an upper end 820 to a lower end 825 through which a suction force can be applied. This suction is produced within the air channel 815 by a negative air pressure sourced external to the pick-up device 805 by an electronic variable air pressure mechanism. With this mechanism, two pre-set values of air pressure, one negative and one positive, can be individually controlled on and off by the robotic device. When a robotic device wants to pick a product, it uses a negative air pressure to secure the product to the pick-up head 140. When the robotic device wants to place a product, it uses a momentary positive air pressure to gently force the product off the pick-up head 140.

In one embodiment, the unique pick-up tip 140 is made of a magnetic material, which allows the electromagnetic end 820 of the pick-up device 805 to attach easily to the pick-up tip 140 at the appropriate time. Further, the pick-up tip's 140 physical design, or configuration, allows it to pick up a specific type and shape of medication. This is a desirable feature of this embodiment, because the pick-up tip's 140 unique design prevents inadvertent placement of the wrong medication in the medicine container or bottle. The pick-up tip 140 has a general "T-shaped" cross-section in that outer perimeter of the upper end 835, or head, is larger than the perimeter of its lower end 840. Additionally, the upper end 835 is comprised of a magnetic material. The pick-up tip 140 has a hollow tube 830 having a channel extending from the upper 820 end to its lower end 840 through which the suction force can be applied. The designs of the lower end 825 of the pick-up device 805 and the upper end 835 of the pick-up tip 140 are such that their respective air channels 815, 830 self-align when the pick-up tip 140 magnetically attaches to the pick-up device 805.

One embodiment of a fulfillment process follows. When a supplier receives an order for a target medication, the type of medication, patient or customer's name, and other salient identifying data are entered into the memory of the fulfillment system. Typically, a supplier may receive multiple orders of the same type of medication for different patients. Thus, an automated fulfillment process as presented herein is particularly advantageous in such situations. A manual operator or automated system places the target medication into the canister's dispensing compartment and the controller verifies the type and amount of medication, as described above. The canister receives an identification code, as discussed above, that matches the type and amount of the medication placed into the canister's dispensing compartment. The supplied canister is taken and placed onto a fulfillment station, as described above, and is scanned into the fulfillment systems memory so the fulfillment system's controller knows the location of the canister, the type of medication that it contains, and the amount of medication within the canister.

As mentioned above, any given fulfillment system may have several fulfillment stations coupled by a conveyor system. However, a labeling station may be located at the starting or input end of the coupled fulfillment stations. The fulfillment system controller instructs the labeling system how to label and identify each medicine bottle. Automated equipment may perform the labeling process. The label or bottle includes ID data, such as a bar code or RFID tag, that matches the ID data of the canister, so that the controller can match the target medication in the canister with the labeled bottle.

After the bottle is properly labeled, it is placed on the conveyor belt, and as it proceeds from one fulfillment station to another, the bottle is scanned or read by an optical scanner or RFID reader and is allowed to pass through, if the bottle's ID data does not match the canister's ID data. It proceeds in this manner from one fulfillment station to a subsequent fulfillment station until it arrives at the fulfillment station that contains the canister whose ID data matches that of the bottle.

When the bottle arrives at the correct station, the above-described system opens the canister, and picks and places the medication in the bottle, until the automated robotic arm places the exact number of tablets or capsules into the labeled bottle. When the bottle is filled with the prescribed number of the target medication, the bottle then proceeds through any remaining fulfillment stations until it reaches an automated sealing station where it is hermetically sealed and capped. If the filled bottle is part of a fulfillment order for any given patients or customer, the controller instructs the robotic arm to place the filled bottle in a buffer area within the sealing station until the remaining portions of the order come through the sealing station. When they do arrive, the controller instructs the system to place the buffered bottle back onto the conveyor. This is advantageous in that the entire order of multiple medications can be easily kept together.

Those skilled in the art to which this application relates will appreciate that other and further additions, deletions, substitutions and modifications may be made to the described embodiments.

What is claimed:

1. A medication fulfillment canister, comprising:
   a bottom section having a tray portion for receiving a medication therein, said tray portion including a front tray portion and a rearward end;
   an upper dispensing compartment slidably engaged with and removably attached to said bottom section and located over at least said rearward end, said upper dispensing compartment having a front end, a rear end, and an opening proximate said front end for allowing a medication to pass therethrough and into said tray portion;
   a tray lid removably attached to said tray portion and adjacent said upper dispensing compartment, said tray lid configured to rotate between an open position and a closed position, wherein said tray lid in said closed position prevents forward movement of said upper dispensing compartment; and
   a lock located within a wall of said bottom section that locks said tray lid in said closed position.

2. The medication fulfillment canister of claim 1, wherein said tray portion is translucent to allow light to pass therethrough.

3. The medication fulfillment canister of claim 1, wherein said tray lid includes one or more lifting surfaces configured to provide a surface whereby a robotic arm can engage and move said tray lid to said open position.

4. The medication fulfillment canister of claim 3, wherein said one or more lifting surfaces are a pair of cantilevered lifting arms that extend over said tray lid and are located on opposing sides of said tray lid.

5. The medication fulfillment canister of claim 1, wherein said bottom section includes one or more notches configured to receive a corresponding post formed in said upper dispensing compartment.

6. The medication fulfillment canister of claim 5, wherein said one or more notches and said post are located on one or opposing sides of said bottom section and said upper dispensing compartment, respectively.

7. The medication fulfillment canister of claim 1 further comprising a pick-up port located in an inner ledge of said bottom section.

8. The medication fulfillment canister of claim 7, wherein said tray lid includes a pick-up tip opening located in a front edge of said tray lid that exposes said pick-up port when said tray lid is in said closed position.

9. The medication fulfillment canister of claim 8 further comprising a pick-up tip seated in said pick-up port.

10. The medication fulfillment canister of claim 9 wherein said pick-up tip has a "T-shaped" cross-section such that an outer perimeter of an upper end of said pick-up tip is larger than a lower end of said pick-up tip, said "T-shaped" cross-section.

11. The medication fulfillment canister of claim 10 wherein said "T-shaped" cross-section has a configuration that allows it to pick-up a predetermined type of medication.

12. The medication fulfillment canister of claim 10 wherein said pick-up tip further has a hollow suction tube having a channel extending from said upper end to said lower end of said pick-up tip.

13. The medication fulfillment canister of claim 1, wherein said lock comprises is a pneumatically actuated lock that includes a pneumatic chamber and an injection port pneumatically coupled to said pneumatic chamber.

14. The medication fulfillment canister of claim 1, wherein at least one of said upper dispensing compartment and said tray lid include identification data that identifies a type of medication located within said upper dispensing compartment and allows a fulfillment systems controller to identify and track said canister through stages of a fulfillment process.

15. The medication fulfillment canister of claim 1, further comprising a feeding gate that is removably attached to said bottom section, said feeding gate reducing a size of said opening to control.

16. The medication fulfillment canister of claim 1 further comprising a mounting rail located on at least one side of said dispensing compartment.

17. The medication fulfillment canister of claim 1 further comprising a pick space located on an underside of said bottom section configured to receive tines of a robotic arm therein.

* * * * *